United States Patent [19]

Frampton et al.

[11] 4,234,748
[45] Nov. 18, 1980

[54] PROCESS FOR THE HYDRATION OF OLEFINS EMPLOYING SLURRIED CATALYST

[75] Inventors: Orville D. Frampton, Wyoming; William R. Birchall, Cincinnati, both of Ohio

[73] Assignee: National Distillers and Chemical Corp., New York, N.Y.

[21] Appl. No.: 52,891

[22] Filed: Jun. 28, 1979

[51] Int. Cl.$^3$ .............................................. C07C 29/04
[52] U.S. Cl. .................................... 568/901; 568/895; 568/896; 568/897; 568/898; 568/899; 568/900
[58] Field of Search ............... 568/895, 896, 897, 898, 568/899, 900, 901

[56] References Cited

U.S. PATENT DOCUMENTS

| | | | |
|---|---|---|---|
| 2,044,414 | 6/1936 | Wilkinson | 568/899 |
| 2,477,380 | 7/1949 | Kreps et al. | 568/899 |
| 2,815,391 | 12/1957 | Taylor | 568/901 |
| 3,164,641 | 1/1965 | Bazzarin | 568/897 |
| 3,328,471 | 6/1967 | Kronig et al. | 568/899 |

*Primary Examiner*—Joseph E. Evans
*Attorney, Agent, or Firm*—Kenneth D. Tremain

[57] ABSTRACT

Olefins such as ethylene and propylene are hydrated in the liquid phase at elevated temperature and superatmospheric pressure to the corresponding alkanols in an aqueous reaction medium containing a catalytically effective amount of at least one substantially water-insoluble olefin hydration catalyst in the form of solid particles substantially uniformly distributed therein.

34 Claims, No Drawings

PROCESS FOR THE HYDRATION OF OLEFINS EMPLOYING SLURRIED CATALYST

This invention relates to the field of olefin hydration processes and, more particularly, to such processes employing substantially water-insoluble catalysts.

The hydration of olefins, e.g., ethylene to ethanol and propylene to n-propanol and isopropanol, employing a variety of metal-containing catalysts is well known. Each of U.S. Pat. Nos. 1,873,536 and 1,907,317 to Brown et al. discloses olefin hydration catalysts containing one or more oxides of aluminum, thorium, titanium, tungsten and chromium. U.S. Pat. No. 1,882,712 to Andrussow et al. discloses the use of oxides of antimony, manganese, tungsten, zinc and/or tin oxides as promotors in metal phosphate ethylene hydration catalysts. U.K. Patent Specification No. 665,214 describes a titania-promoted tungsten oxide olefin hydration catalyst. U.S. Pat. No. 1,977,633 to Horsley acknowledges that it is known to employ compounds of gold, iron, chromium, vanadium, tungsten, molybdenum and manganese for olefin hydration. U.S. Pat. No. 2,162,913 to Eversole et al., U.S. Pat. No. 2,173,187 to Tanner and U.S. Pat. No. 2,798,097 to Hettinger, Jr., et al. each describes the use of a water-soluble catalyst such as phosphotungstic acid in the hydration of olefins. U.S. Pat. No. 2,769,847 to Robinson describes a binary metal oxide hydration catalyst in which ferric oxide is in intimate admixture with titania. According to U.S. Pat. No. 2,815,391 to Taylor, olefin is hydrated in the presence of stirred catalyst particles and the product ethanol is recovered through filters which retain the catalyst particles in the reaction medium. The filters are provided with means for reversing the flow of liquid therethrough so that the catalyst particles deposited on the filters are detached and washed back into the reaction area. Taylor prefers to maintain a high proportion of catalyst particles in the lower part of the reaction medium with a low proportion of catalyst particles in the upper part of the reaction medium so as to reduce the amount of catalyst reaching the filters and the frequency with which the latter must be freed of accumulated material. The olefin hydration process of U.S. Pat. No. 2,995,609 to Frech et al. employs a fixed bed molybdenum oxide olefin hydration catalyst. The related olefin hydration catalyst of U.S. Pat. No. 3,076,036 to Hansen is made up of molybdenum oxide in combination with silica and an oxide such as alumina, hafnia, zirconia, titania or thoria. The olefin hydration process of U.S. Pat. No. 3,705,912 to Massie employs a hexavalent molybdenum compound. The olefin hydration process of U.S. Pat. No. 3,452,106 to Sato et al. employs a fixed bed catalyst containing a blue oxide of tungsten with an oxide of chromium as a binding agent. U.S. Pat. Nos. 3,678,118 and 3,801,656 to Frampton disclose fixed bed olefin hydration catalysts containing zirconia-supported blue tungsten oxide and molybdenum oxide, respectively. The fixed bed, strongly acidic ion exchange resin olefin hydration catalyst disclosed in U.S. Pat. No. 3,994,983 to Webers et al. behaves as a porous mass permitting free flow of olefin reactant therethrough.

In accordance with the present invention, olefins are hydrated in the liquid phase at elevated temperature and superatmospheric pressure to the corresponding alkanols in an aqueous reaction medium containing a catalytically effective amount of at least one substantially water-insoluble olefin hydration catalyst in the form of solid particles substantially uniformly distributed therein. The invention contemplates the use of a conventional high pressure olefin hydration reactor provided with the usual controls, piping, etc.

The olefin hydration process herein possesses several advantages over the prior art procedures, supra. By maintaining the solid catalyst particles substantially uniformly distributed throughout the entire reaction medium and avoiding any significant localization of catalyst concentration therein, optimum exposure of available catalyst surface area to reactants is achieved in the present invention and higher and faster rates of olefin conversion are promoted.

The olefins which can be hydrated in accordance with the process of this invention contain from 2 to about 30 carbon atoms and include both mono- and polyolefinic compounds, e.g., ethylene, propylene, 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene, 5-decene, 3-methyl-1-butene, 3-methyl-1-pentene, 3-methyl-2-pentene, 3-methyl-1-hexene, 3-methyl-1-heptene, 4-methyl-2-heptene, 3-methyl-1-octene, 1,3-butadiene, 1,3-pentadiene, 1,3-hexadiene, 2,4-hexadiene, 1,3-heptadiene, 2,4-heptadiene, 1,3-octadiene, 2,4-octadiene, 4-methyl-1,3-hexadiene, etc.

Any of the substantially water-insoluble catalysts heretofore used in olefin hydration processes can be employed herein with or without the use of supports and in the presence or absence of promotors. The catalyst is provided in the form of particles, e.g., particles having average particle Martin diameters of from about 15 microns to about 1.5 cm and preferably from about 25 microns to about 0.01 cm. Martin diameter is the distance between opposite sides of the particle, measured crosswise of the particle and on a line bisecting the projected area as described by Martin et al, Trans. Ceram. Soc. (Eng.) 23, 61 (1924). Suitable catalysts include molybdenum oxide, blue tungsten oxide and either or both of these oxides deposited upon a solid catalyst support such as titania or zirconia. Especially advantageous for use herein are the binary, ternary and other mixed metal oxide olefin hydration catalysts disclosed in commonly assigned, copending U.S. patent application Ser. No. 433,168 filed Jan. 14, 1974). These catalysts are interacted oxide compositions of at least one metal oxide having an electronegativity value $X_i$ for the metal ion above about 20.0 with at least one different metal oxide having an electronegativity value $X_i$ for its metal ion above about 13.0, electronegativity of the metal ion being calculated by the equation $X_i = (1+2z)X_o$ in which z is the charge on the metal ion and $X_o$ is the electronegativity value of the neutral metal atom as assigned by Pauling (and given in such standard reference works as Lange's *Handbook of Chemistry*, eleventh edition). As "interacted oxide compositions", the constituent metal oxides making up the catalysts are more closely associated with one another than would be possible through mere mechanical mixing. Examples of such catalysts include mixed metal oxides containing at least two metal oxides of the group: $MoO_3$, $WO_3$, $W_4O_{11}$, $TeO_2$, $TeO_3$, $AuO_2$, $CrO_3$ and $Sb_2O_5$, each of which has an electronegativity value $X_i$ for the metal ion above about 20.0, and mixed metal oxides containing at least one of the metal oxides of the aforesaid group and at least one metal oxide of the group; $TiO_2$, $Fe_2O_3$, $MnO_2$, $SnO_2$, $SiO_2$, $MoO_2$, $WO_2$, $V_2O_5$, $VO_2$, $Ta_2O_5$, $RuO_2$, $Rh_3O_3$, $RhO_2$, $ReO_2$, $ZnO_2$, $CrO_2$, $B_2O_3$, $Sb_2O_3$ and $ZrO_2$, each of which has an electronegativity value $X_i$ for the metal ion above about 13.0 but below about 20.0. According to one method for preparing these mixed metal oxide catalysts, aqueous solutions of the selected metals in the form of their water-soluble salts, e.g., the halides, nitrates, phosphates, etc. are contacted with a base such as ammonia with consequent coprecipitation of the metal oxides. The oxides are separated from the supernatant, dried and if desired, calcined in a non-reducing atmosphere. Another method ("slurry growth") which can be employed herein for preparing these catalysts calls for heating an aqueous slurry of the selected oxides, precipitating the interacted oxides from the liquid phase as reported in Batist, et al. *J. Cat.* Vol. 12, pp. 45–60 (1968), and calcining the dried precipitated oxides in a non-reducing atmosphere. Especially preferred is a catalyst prepared by chemically interacting $MoO_3$ with a metal oxide of the group: $Sb_2O_5$, $Fe_2O_3$, $V_2O_5$, $Bi_2O_3$, $ZrO_2$ and $ZnO_2$.

Still other substantially water-insoluble olefin hydration catalysts which can be used to good advantage herein are the following:

A. Mixed oxides in which the atomic ratio among the constituent metallic elements, Co:Fe:Bi:W:Mo:Si:Z is within the range of 2.0–20.0:0.1–10.0:0.1–10.0:0.5–10.0:2.0–11.5:0.5–15.0:0.005–1.0, with the proviso that W+Mo=12, and Z is an alkali metal. The mixed oxides are suitably prepared in accordance with procedures described in U.S. Pat. No. 3,825,600 and can, if desired, be applied to a solid carrier such as silica gel, titania, zirconia, alumina, porous glass beads, celite, silicon carbide, diatomaceous earth, etc.

B. The oxide obtained from the thermal decomposition of ammonium molybdo-6-cobaltate III. Thus, the cobaltate which has the formula $(NH_4)_6[Co_2Mo_{10}O_{34}(OH)_4].5H_2O$ is heated in the range of from about 450° C. to about 525° C. or even higher for from about 8 to about 48 hours. If desired, the cobaltate can be applied from an aqueous solution to a porous inert support such as steam hardened silica gel which is thereafter dried and heated in the aforesaid manner. Optionally, aqueous solutions of ammonium molybdo-6-cobaltate III can be combined with one or more aqueous solutions of other metal salts such as $Bi(NO_2)_3$ and following drying, heated as stated.

C. Ternary mixed oxides of the composition $MoO_3$-$TiO_2$-$SiO_2$ prepared by depositing the binary oxide $TiO_2$-$MoO_3$ having a range of atomic ratios Mo/(Ti+Mo) of from about 0.4 to 0.7 upon a silica gel support.

D. At least one metal oxide having an electronegativity value $X_i$ for the metal ion above about 20.0, e.g., any of those recited above, in interacted relationship with a single oxide, binary oxide, ternary oxide or other mixed oxide having an electronegativity $X_i$ for its metal ion(s) below about 13. Examples of metal oxides having an electronegativity value $X_i$ for the metal ion below about 13 include $HfO_2$ and $ThO_2$.

E. Molybdenum oxide, $MoO_3$, mechanically admixed with, and spread out upon the surface of a single oxide, binary oxide, ternary oxide or other mixed oxide, of the following metallic elements: Ti, Zr, Hf, Th, Sb, Cr and W.

F. Molybdenum oxides and/or hydroxides prepared by the solid phase reduction of $MoO_3$ with other lower valence metals such as MoO and $MoO_2$ at elevated temperatures in a closed system, or by reduction of a metal molybdate with trivalent molybdenum in aqueous solution at ambient temperature. Examples of the reduced molybdenum oxides and hydroxides include $Mo_{17}O_{47}$, $Mo_5O_{14}$, $Mo_8O_{23}$, $Mo_{18}O_{52}$, $Mo_9O_{26}$, $Mo_4O_{10}(OH)_2$ and $Mo_8O_{23}.xH_2O$.

G. Iron defective iron molybdate in which the ratio of molybdenum to iron is greater than stoichiometric, e.g., greater than 1.7.

H. The reaction product of bismuth molybdate with an iron compound such as Fe(III) hydroxide. Especially advantageous are such reaction products in which the atomic ratios Bi:Fe:Mo are 1:1:1 and 3:1:2.

I. Bismuth molybdate, $Bi_2O_5$-$MoO_3$

J. Oxides obtained from the thermal decomposition of ammonium salts having a heteropolymolybdate anion in which the central metallic ion is $Co^{+3}$, $Fe^{+3}$, $Cr^{+3}$, $Al^{+3}$, $Ni^{+2}$, $Ni^{+4}$, or $Mn^{+4}$. The ammonium salts are decomposed by heating in the range of from about 450° C. to about 525° C. or even higher for from about 8 to about 48 hours. Examples of such ammonium salts include ammonium-9-molybdonickelate IV, ammonium-6-molybdonickelate II, ammonium-6-molybdochromate III, ammonium-6-molybdoaluminate III, ammonium-6-molybdoferrate III, ammonium-5-molybdocobaltate III, and ammonium-9-molybdomanganate IV. If desired, the ammonium salts can be combined with other metal salts prior to decomposition and/or the ammonium salts can be deposited upon a solid, inorganic carrier such as silica gel prior to thermal treatment.

The catalyst is advantageously prereduced, preferably with hydrogen at a temperature of about 350°–500° C. An alkanol vapor such as ethanol, isopropanol, butanol, and the like, can also be effectively used to prereduce the catalyst.

In accordance with the invention, the catalyst is maintained in an aqueous olefin hydration reaction medium substantially uniformly distributed therein. Such uniform distribution is most conveniently achieved by keeping the reaction medium in a constant state of agitation, preferably by mechanical stirring or by continuously circulating a portion of the reaction medium from the top to the bottom of the olefin hydration reactor.

To facilitate stirring, a suitable surface active agent is advantageously incorporated into the reaction medium, for example, at a level of from about 0.1 to about 2 weight percent. Suitable surface active agents include the "Igepals" (G.A.F.), the "Tweens" (Atlas Chemical) and the "Pluronics" (BASF Wyandotte). The "Ingepals" are members of a homologous series of alkylphenoxypoly (ethyleneoxy) ethanols which can be represented by the general formula

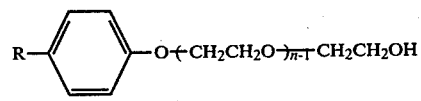

wherein R represents an alkyl radical and n represents the number of mols of ethylene oxide employed, among which are alkylphenoxypoly (ethyleneoxy) ethanols having alkyl groups containing from about 7 to about 18 carbon atoms, inclusive, and having from about 4 to about 100 ethyleneoxy units, such as the heptylphenoxypoly (ethyleneoxy) ethanols, nonylphenoxypoly (ethyleneoxy) ethanols and dodecylphenoxypoly (ethyleneoxy) ethanols; the sodium or ammonium salts of the sulfate esters of these alkylphenoxypoly (ethyleneoxy) ethanols, alkylpoly (ethyleneoxy) ethanols; alkylpolypropyleneoxy) ethanols; octylphenoxyethoxyethyldimethylbenzylammonium chloride; polyethylene glycol t-dodecylthioether. The "Tweens" are polyoxyalkylene derivatives of fatty acid partial esters of sorbitol anhydride, such as the polyoxyalkylene derivatives of sorbitan monolaurate, sorbitan monopalmitate, sorbitan monostearate, sorbitan tristearate, sorbitan monooleate and sorbitan trioleate. The "Pluronics" are condensates of ethylene oxide with a hydrophobic base formed by condensing propylene oxide with propylene glycol, and the like. Other suitable surface active agents which can be employed herein are ethylene oxide derivatives of long chain fatty alcohols such as octyl, dodecyl, lauryl or cetyl alcohol. Those skilled in the art will recognize still other surface active agents which can be used for the stated purpose.

In the steady-state operation of the process, any catalyst which is withdrawn from the reactor as part of a product recovery stream will be restored to the reactor at the same rate by a catalyst recycle stream (containing fresh water as needed) thus insuring a fairly constant level of catalyst for the hydration reaction even while product alkanol is being removed.

The reaction system is held at a temperature sufficiently high to achieve activity in the catalyst and at a pressure as high as practicable for optimum olefin solubility and at a mole ratio of water to olefin sufficiently high at this operating pressure to maintain aqueous liquid phase. An increase in mole ratio results in increased amounts of liquid phase in the system. This allows for increased solution of alkanol from the vapor phase; however an economical optimum upper ratio limit exists since too high a ratio will result in excessive dilution of the alkanol.

Conditions of hydration should be such that there is always present a liquid phase into which water, olefin and alkanol can dissolve. The liquid phase can be either water or an aqueous solution of an inert, relatively non-volatile or, where volatile, easily separable by distillation, liquid solvent. Various ketones, aldehydes, alkanols, nitriles, esters, amides, amino alcohols, phenols, triols, polyols, alkanol ethers, and amines may be employed as inert solvents. Examples of suitable solvents include ethylene glycol, hexylene glycol (2-methyl-2,4-pentane diol) dipropylene glycol, tetraethylene glycol, propylene glycol, ethylene diamine, glyoxal, isopropyl alcohol, methyl cellosolve, morpholine, triethanolamine, acetone, tert- butyl alcohol, acetonitrile, methyl ethyl ketone, ethyl acetate and ethanol itself. Such solvents achieve a higher solubility of the alkanol compared to water and at the same time dissolves the alkanol and by-product ether. These factors increase hydration rate, allow for use of lower pressures, and drive the hydration to high olefin conversions. After the product alkanol has been separated from it, the selected solvent can be recycled. When ethanol itself is the selcted solvent, only that amount of alkanol synthesized is taken as product and the remainder recycled.

Catalytic hydration with the above catalysts may be conducted over a wide range of conditions. Usually the temperature employed is within the range of about 250°–350° C., with a preferred range of about 290°–310° C. The pressure should be within the range of 750 to 15,000 psi and preferably should be between 3500 and 4500 psi. The mole ratio of water to olefin is generally within the range of 1:5 to 25:1, and preferably it is within the range of 8:1 to 15:1. Amounts of catalyst used can range from about 10 to about 4,000 gm per liter of reaction medium with from 100 to 3500 gm catalyst per liter of reaction medium being preferred. As one approaches the higher end of this range, the catalyst slurry is very dense yet capable of being pumped and maintained in a state of substantially uniform suspension. High catalyst concentrations are, of course, favored as promoting high rates of alkanol production. Prior art processes employing filters for the removal of product alkanol virtually preclude the use of highly concentrated catalyst slurries due to the practical difficulty of keeping the filters clear and functioning.

The product alkanol can be separated from the reaction medium without appreciably disturbing the uniform distribution of the catalyst particles therein by continuously or intermittently withdrawing a portion of the reaction medium containing suspended catalyst and ethanol through a pressure let-down or expansion valve to simultaneously flash off a quantity of water, alkanol, unreacted olefin and volatile by-products and cool the portion of reaction medium so withdrawn. The vapor flash-off is put through a condenser, the aqueous alkanol condensate being subjected to distillation for recovery of the alkanol at the desired level of concentration and the remaining vapors, largely unreacted olefin, being re-compressed to reaction pressure and recycled to the reactor. The catalyst slurry together with makeup water as needed is also compressed to reaction pressure and recycled to the reactor. Alternatively or in addition to this procedure for separating product alkanol from the reaction medium, the vapors above the reaction medium containing alkanol and any unreacted olefin and/or low-boiling reaction by-product such as ether are continuously or intermittently withdrawn through an expansion valve and the expanded, cooled vapor is passed through a low pressure water absorber which absorbs the alkanol. The vapor overhead containing unreacted olefin and any other gaseous material is re-compressed to reaction pressure and returned to the reaction. The aqueous alkanol from the absorber is subjected to distillation for recovery of the alkanol at the desired level of concentration.

EXAMPLES 1 TO 11

In the examples whose results are set forth below, a valved 10 ml stainless steel reactor wrapped with heating wire and having a dual thermocouple for measurement and control of temperature was employed for the hydration of ethylene at moderate pressure with various aqueous solid catalyst suspensions. The contents of the reactor were maintained in a substantially uniformly distributed suspension by constant shaking of the reactor in a direction perpendicular to its side. Travel distance was 1.5 inches and the shaking rate was 300 cycles per minute. The reactor was charged with 1 g catalyst, 4.5 g water and 800 psig olefin at room temperature, then rapidly heated to 300° C. reaction temperature while being shaken as described. After reaction, the shaking was stopped, the reactor cooled rapidly (with solid carbon dioxide) and its contents analyzed. The results were as follows:

Ethylene Hydration at Moderate Pressure[1]

| Example No. | Catalyst | Ethanol Rate g[2] | Yield %[3] |
|---|---|---|---|
| 1 | ⅛" pellets of 18.9% $WO_3$ on titania reduced with $H_2$ at 400° C. | .036 | 1.7 |
| 2 | 17% $MoO_3$ . $TiO_2$ on silica gel with Mo/(Mo + Ti) = .54 | .16 | 7.3 |
| 3 | "Iron defective"[4] Iron molybdate | .14 | 6.4 |
| 4 | $Sb_2O_5$ . $MoO_3$[5] with Mo/(Mo + Sb) = .5 | .14 | 6.4 |
| 5 | $Sb_2O_5$ . $MoO_3$[6] with Mo/(Mo + Sb) = .5 | .11 | 5.0 |
| 6 | $SnO_2$ . $MoO_3$[5] with Mo/(Mo + Sn) = .5 | .11 | 5.0 |
| 7 | $V_2O_5$ . $MoO_3$[5] | .056 | 2.6 |
| 8 | $Bi_2O_3$ . $MoO_3$[5] | .086 | 3.9 |
| 9 | $Z_rO_2$ . $MoO_3$[7] with $Z_rO_2$:$MoO_3$ = 3.08 | .06 | 2.8 |
| 10 | $Bi_2O_3$ . $Fe_2O_3$ . $MoO_3$ with Bi:Fe:Mo = 2:1:3 | .056 | 2.6 |
| 11 | $Bi_2O_3$ . $Fe_2O_3$ . $MoO_3$ with Bi:Fe:Mo = 1:1:1 | .076 | 3.5 |

[1]Total pressure, reaction temperature, time, mole ratio $H_2O$:$C_2H_4$, catalyst weight, and volume, $H_2O$ weight, $C_2H_4$ volume, $C_2H_4$ pressure at 70° F. were: 4000 psi, 300° C., 30 minutes, 10.5, 1 gram, .17 cc, 4.5 grams, 5.33 cc, 800 psi.
[2]"g" refers to grams alcohol/gram catalyst/hr
[3]Theoretical maximum is 1.09 g alcohol
[4]Described in J. Catalysis 16 321-25 (1970)
[5]Prepared by slurry growth of the oxide followed by calcination.
[6]Prepared by slurry growth of $Sb_2O_5$ in ammonium molybdate followed by drying and calcination at 500° C.
[7]Prepared by coprecipitation of $ZrOCl_2$ and ammonium molybdate followed by calcination at 600° C.

EXAMPLES 12 TO 23

In Examples 12 to 23, the same reaction and procedure (heating, shaking and cooling) were used as in Examples 1 to 11 except at higher pressure. However, the reactant charge was changed as shown in footnote 1 of the following table.

ETHYLENE HYDRATION AT HIGH PRESSURE[1]

| Example No. | Catalyst | Ethanol rate g[2] | yield %[3] |
|---|---|---|---|
| 12 | $ThO_2$ promoted catalyst of Example 1 | .17 | 2.5 |
| 13 | $ThO_2$ promoted catalyst of Example 1 | .17 | 2.5 |
| 14 | $ThO_2$ promoted catalyst of Example 1 | .23 | 3.4 |
| 15 | $ThO_2$ promoted catalyst[5] of Example 1 | .22 | 9.2 |
| 16 | Mixed Oxides[4] | .54 | 8.0 |
| 17 | Mixed Oxides[4] | .47 | 7.1 |
| 18 | Mixed Oxides[4] | .56 | 8.4 |
| 19 | Mixed Oxides[4] | .64 | 9.6 |
| 20 | Mixed Oxides[4] | .56 | 8.4 |
| 21 | Sb:W = 1:19 | .27 | 13 |
| 22 | Sb:W = 1:1 | .30 | 14 |
| 23 | Sb:W = 1:1[6] | .27 | 8.0 |

[1]Total pressure, reaction temp. and time, mole ratio $H_2O$:$C_2H_4$, catalyst wt. and vol., $H_2O$ wt., $C_2H_4$ vol. and pressure at 70° F. were: 14745 psi, 300° C., 30 min., 3.06, 1g, .17 cc, 4 g, 5.83 cc, 1500 psi resp.
[2]"g" refers to grams alcohol/gram catalyst/hr.
[3]theoretical maximum is 3.34 g.
[4]$Co_4FeBiW_2Mo_{10}Si_{1.35}K_{06}$
[5]wt. used was 2.8 g instead of 1.0 g
[6]wt. used was 0.63 g instead of 1.0 g

EXAMPLES 24 TO 42

Employing the olefin hydration reactor and procedure (heating, shaking and cooling) of Examples 1 to 11, the effects of suspended MoO, catalyst weight and reaction time on the conversion of ethylene to ethanol and the effect of catalyst reuse after an extended time of reaction were as follows:

ETHYLENE HYDRATION RATES FOR $MoO_3$
Reaction Conditions: 4.5 g $H_2O$; 300° C.; 4000 psi

| Example No. | Catalyst g | Time min. | Ethanol Produced g |
|---|---|---|---|
| 24 | 0.25 | 60 | .104 |
| 25 | 0.5 | 15 | .01 |
| 26 | | 30 | .05 |
| 27 | | 45 | .08 |
| 28 | | 60 | .11 |
| 29 | | 75 | .13 |
| 30 | | 360 | .15 |
| 31 | 1.0 | 15 | tr. |
| 32 | | 30 | .04 |
| 33 | | 60 | .11 |
| 34 | | 300 | .15[1] |
| 35 | | 15 | .01 |
| 36 | | 30 | .05 |
| 37 | | 45 | .07 |
| 38 | | 60 | .11 |
| 39 | | 320 | .14[1] |
| 40 | 5.0 | 30 | .015 |
| 41 | 9.0 | 30 | .01 |
| 42 | 1.0[2] | 330 | .05 |

[1]Inactive on reuse
[2]Catalyst of Example 1

These data show that 0.25 g $MoO_3$ were as productive as 2.0 g for one hour use. However, on reuse after five hours, the catalyst had lost activity evidently because it had been reduced to an inactive form.

What is claimed is:

1. A process for the liquid phase hydration of olefin to the corresponding alkanol in an olefin hydration reactor which comprises hydrating olefin at elevated temperature and superatmospheric pressure in an aqueous reaction medium containing a catalytically effective amount of at least one substantially water-insoluble olefin hydration catalyst in the form of solid particles substantially uniformly distributed throughout the entire reaction medium to provide an aqueous reaction medium containing alkanol, unreacted olefin and suspended catalyst, continuously or intermittently withdrawing a portion of the reaction medium through an expansion valve to simultaneously flash off alkanol and unreacted olefin and cool the residual aqueous catalyst suspension, and cooling the flash-off vapors to condense the alkanol as dilute aqueous alkanol.

2. The process of claim 1 in which the olefin is ethylene.

3. The process of claim 1 in which the catalyst is selected from the group consisting of molybdenum oxide, blue tungsten oxide, zirconia-supported molybdenum oxide and zirconia-supported blue tungsten oxide.

4. The process of claim 1 in which the catalyst is selected from the group consisting of:
   (a) a mixed metal oxide wherein each metal oxide has an electronegativity value $X_i$ for its metal ion above about 20.0 and,
   (b) a mixed metal oxide wherein at least one metal oxide has an electronegativity value $X_i$ for its metal ion above about 20.0 and at least one metal oxide has an electronegativity value $X_i$ for the metal ion above about 13.0 but not above about 20.0.

5. The process of claim 4 in which catalyst (a) is $MoO_3$, $WO_3$, $W_4O_{11}$, $TeO_3$, $CrO_3$ or $Sb_2O_5$, and catalyst (b) is $TiO_2$, $Fe_2O_3$, $MnO_2$, $SnO_2$, $SiO_2$, $MoO_2$, $WO_2$, $V_2O_5$, $VO_2$, $Ta_2O_5$, $RuO_2$, $Rh_2O_3$, $RhO_2$, $ReO_2$, $Bi_2O_3$, $Sb_2O_3$ or $ZrO_2$.

6. The process of claim 1 in which the temperature of the hydration reaction is from about 250° C. to about 350° C.

7. The process of claim 1 in which the pressure at which the hydration reaction is carried out is from about 750 to about 15,000 psi.

8. The process of claim 1 in which the pressure at which the hydration reaction is carried out is from about 3500 to about 4500 psi.

9. The process of claim 1 in which the mole ratio of water to olefin is from about 1:5 to about 25:1.

10. The process of claim 1 in which the solid particles have average particle Martin diameters of from about 15 microns to about 1.5 cm.

11. The process of claim 1 in which the solid particles have average particle Martin diameter of from about 25 microns to about 0.1 cm.

12. The process of claim 1 in which from about 0.5 to about 100 gm catalyst per liter of reaction medium is employed.

13. The process of claim 1 in which uniform distribution of catalyst particles in the reaction medium is achieved by mechanical stirring.

14. The process of claim 1 in which uniform distribution of catalyst particles is achieved by continuously recirculating a portion of the reaction medium from the bottom to the top of the reactor.

15. The process of claim 13 in which stirring is facilitated by the addition of a surface active agent to the reaction medium.

16. The process of claim 1 in which catalyst is present at a level of from about 10 to about 4000 gm per liter of reaction medium.

17. The process of claim 16 in which the catalyst is present at a level of from about 100 to about 3500 gm per liter of reaction medium.

18. A process for the liquid phase hydration of olefin to the corresponding alkanol in an olefin hydration reactor which comprises hydrating olefin at elevated temperature and super-atmospheric pressure in an aqueous reaction medium containing a catalytically effective amount of at least one substantially water-insoluble olefin hydration catalyst in the form of solid particles substantially uniformly distributed throughout the entire reaction medium to provide an aqueous reaction medium containing alkanol, unreacted olefin and suspended catalyst, continuously or intermittently withdrawing alkanol-containing vapor above the reaction medium through an expansion valve and passing the expanded, cooled vapor through a low pressure water absorber to absorb the alkanol and provide dilute aqueous alkanol.

19. The process of claim 18 in which the olefin is ethylene.

20. The process of claim 18 in which the catalyst is selected from the group consisting of molybdenum oxide, blue tungsten oxide, zirconia-supported molybdenum oxide and zirconia-supported blue tungsten oxide.

21. The process of claim 18 in which the catalyst is selected from the group consisting of:
 (a) a mixed metal oxide wherein each metal oxide has an electronegativity value $X_i$ for its metal ion above about 20.0 and,
 (b) a mixed metal oxide wherein at least one metal oxide has an electronegativity value $X_i$ for its metal ion above about 20.0 and at least one metal oxide has an electronegativity value $X_i$ for the metal ion above about 13.0 but not above about 20.0.

22. The process of claim 21 in which catalyst (a) is $MoO_3$, $WO_3$, $W_4O_{11}$, $TeO_3$, $CrO_3$ or $Sb_2O_5$, and catalyst (b) is $TiO_2$, $Fe_2O_3$, $MnO_2$, $SnO_2$, $SiO_2$, $MoO_2$, $WO_2$, $V_2O_5$, $VO_2$, $Ta_2O_5$, $RuO_2$, $Rh_2O_3$, $RhO_2$, $ReO_2$, $Bi_2O_3$, $Sb_2O_3$ or $ZrO_2$.

23. The process of claim 18 in which the temperature of the hydration reaction is from about 250° C. to about 350° C.

24. The process of claim 18 in which the pressure at which the hydration reaction is carried out is from about 750 to about 15,000 psi.

25. The process of claim 18 in which the pressure at which the hydration reaction is carried out is from about 3500 to about 4500 psi.

26. The process of claim 18 in which the mole ratio of water to olefin is from about 1:5 to about 25:1.

27. The process of claim 18 in which the solid particles have average particle Martin diameters of from about 15 microns to about 1.5 cm.

28. The process of claim 18 in which the solid particles have average particle Martin diameter of from about 25 microns to about 0.1 cm.

29. The process of claim 18 in which from about 0.5 to about 100 gm catalyst per liter of reaction medium is employed.

30. The process of claim 18 in which uniform distribution of catalyst particles in the reaction medium is achieved by mechanical stirring.

31. The process of claim 18 in which uniform distribution of catalyst particles is achieved by continuously recirculating a portion of the reaction medium from the bottom to the top of the reactor.

32. The process of claim 30 in which stirring is facilitated by the addition of a surface active agent to the reaction medium.

33. The process of claim 18 in which catalyst is present at a level of from about 10 to about 4000 gm per liter of reaction medium.

34. The process of claim 33 in which the catalyst is present at a level of from about 100 to about 3500 gm per liter of reaction medium.

* * * * *